US011240968B2

United States Patent
Hunter et al.

(10) Patent No.: US 11,240,968 B2
(45) Date of Patent: Feb. 8, 2022

(54) POLLEN DISTRIBUTION SYSTEM FOR AN INDOOR GARDENING APPLIANCE

(71) Applicant: Haier US Appliance Solutions, Inc., Wilmington, DE (US)

(72) Inventors: Matthew Hunter, Louisville, KY (US); Michael Goodman Schroeder, Louisville, KY (US); David C. McCalpin, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 132 days.

(21) Appl. No.: 16/580,189

(22) Filed: Sep. 24, 2019

(65) Prior Publication Data
US 2021/0084827 A1 Mar. 25, 2021

(51) Int. Cl.
*A01G 2/00* (2018.01)
*A01G 13/02* (2006.01)
*A01H 1/02* (2006.01)

(52) U.S. Cl.
CPC .............. *A01G 2/00* (2018.02); *A01G 13/02* (2013.01); *A01H 1/027* (2021.01)

(58) Field of Classification Search
CPC ... A01G 2/00; A01G 7/06; A01G 9/18; A01G 9/26; A01G 31/00; A01G 31/02; A01G 9/24; A01G 31/0206; A01G 31/0243; A01G 31/04; A01G 31/043; A01G 2013/004; A01G 2013/046; A01H 1/027
USPC ........................................................ 47/1.41
See application file for complete search history.

(56) References Cited

U.S. PATENT DOCUMENTS

| | | | |
|---|---|---|---|
| 2,660,002 A * | 11/1953 | Farley | A01H 1/027 47/1.41 |
| 5,956,897 A | 9/1999 | Takashima | |
| 7,832,142 B1 | 11/2010 | Olson | |
| 8,869,447 B2 | 10/2014 | Benfey et al. | |
| 9,357,714 B2 | 6/2016 | Van Der Knaap et al. | |
| 9,974,243 B2 | 5/2018 | Martin | |
| 10,055,117 B2 | 8/2018 | Kim et al. | |
| 2018/0042186 A1 * | 2/2018 | Kop | A01H 1/027 |
| 2019/0029201 A1 | 1/2019 | Griffin | |
| 2019/0075741 A1 | 3/2019 | Olesen et al. | |

(Continued)

FOREIGN PATENT DOCUMENTS

| | | |
|---|---|---|
| CN | 105519424 A | 4/2016 |
| CN | 205756216 U | 12/2016 |

(Continued)

*Primary Examiner* — David J Parsley
*Assistant Examiner* — Danielle A Clerkley
(74) *Attorney, Agent, or Firm* — Dority & Manning, P.A.

(57) ABSTRACT

An indoor gardening appliance includes a liner defining a grow chamber and a grow module rotatably mounted within the grow chamber and defining a plurality of apertures for receiving a plurality of plant pods. A pollen pod is mounted to the grow module in one of the apertures and contains pollen for pollinating the plant pods to facilitate plant growth. A pollen ejection device, which may be a pressurized air nozzle or a protruding member for puncturing the pollen pod, is fixed to the liner or otherwise stationary relative to the pollen pod and is configured for engaging the pollen pod when the grow module rotates the pollen pod past the pollen ejection device to discharge and disperse pollen onto the plant pods.

20 Claims, 10 Drawing Sheets

(56) References Cited

U.S. PATENT DOCUMENTS

2019/0082620 A1  3/2019  Griffin
2019/0114935 A1  4/2019  Nolan et al.

FOREIGN PATENT DOCUMENTS

| CN | 206165391 U | 5/2017 |
| CN | 108651075 A | 10/2018 |
| JP | 2012085586 A | 5/2012 |
| KR | 101954237 B1 | 3/2019 |
| RU | 2061371 C1 | 6/1996 |
| RU | 2127874 C1 | 3/1999 |
| WO | WO2012100482 A1 | 8/2012 |
| WO | WO2018068042 A1 | 4/2018 |
| WO | WO2018158093 A1 | 9/2018 |

\* cited by examiner

POLLEN DISTRIBUTION SYSTEM FOR AN INDOOR GARDENING APPLIANCE

FIELD OF THE INVENTION

The present subject matter relates generally to systems for gardening plants indoors, and more particularly, to systems and methods of pollen distribution within an indoor gardening appliance.

BACKGROUND OF THE INVENTION

Conventional indoor garden centers include a cabinet defining a grow chamber having a number of trays or racks positioned therein to support seedlings or plant material, e.g., for growing herbs, vegetables, or other plants in an indoor environment. In addition, such indoor garden centers may include an environmental control system that maintains the growing chamber at a desired temperature or humidity. Certain indoor garden centers may also include hydration systems for watering the plants and/or artificial lighting systems that provide the light necessary for such plants to grow.

Certain indoor garden centers include stationary racks or trellises that are designed for receiving plant pods that may contain plant seeds and/or flowers. Pollination is typically desirable to create new seeds, new plants, and a generally healthy ecosystem within which plants may thrive. However, pollination in indoor garden centers has typically been achieved by manual dispersion of pollen by the user or gardener using the garden center. Manual pollination is typically inefficient, time-consuming, costly, and results in uneven pollination and new plant growth. Thus, conventional pollination systems require significant user interaction and manipulation and are limited in effectiveness.

Accordingly, an improved indoor garden center would be useful. More particularly, an indoor garden center with a pollen distribution system that disperses pollen to desired locations at desired times to support a healthy ecosystem of plants would be particularly beneficial.

BRIEF DESCRIPTION OF THE INVENTION

Aspects and advantages of the invention will be set forth in part in the following description, or may be apparent from the description, or may be learned through practice of the invention.

In one exemplary embodiment, a gardening appliance is provided, including a liner positioned within a cabinet and defining a grow chamber and a grow module mounted within the liner, the grow module including a central hub rotatable about an axis and a plurality of partitions extending from the central hub substantially along a radial direction to define a plurality of grow chambers spaced apart along a circumferential direction. An aperture is defined in the grow module for receiving a pollen pod containing pollen and a pollen ejection device is configured for engaging the pollen pod to disperse a portion of the pollen.

In another exemplary embodiment, a pollen distribution system for a gardening appliance is provided. The gardening appliance includes a liner defining a grow chamber. The pollen distribution system includes a grow module rotatably mounted within the grow chamber and defining an aperture for receiving a pollen pod containing pollen and a pollen ejection device is configured for engaging the pollen pod to disperse a portion of the pollen.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Figure 1:
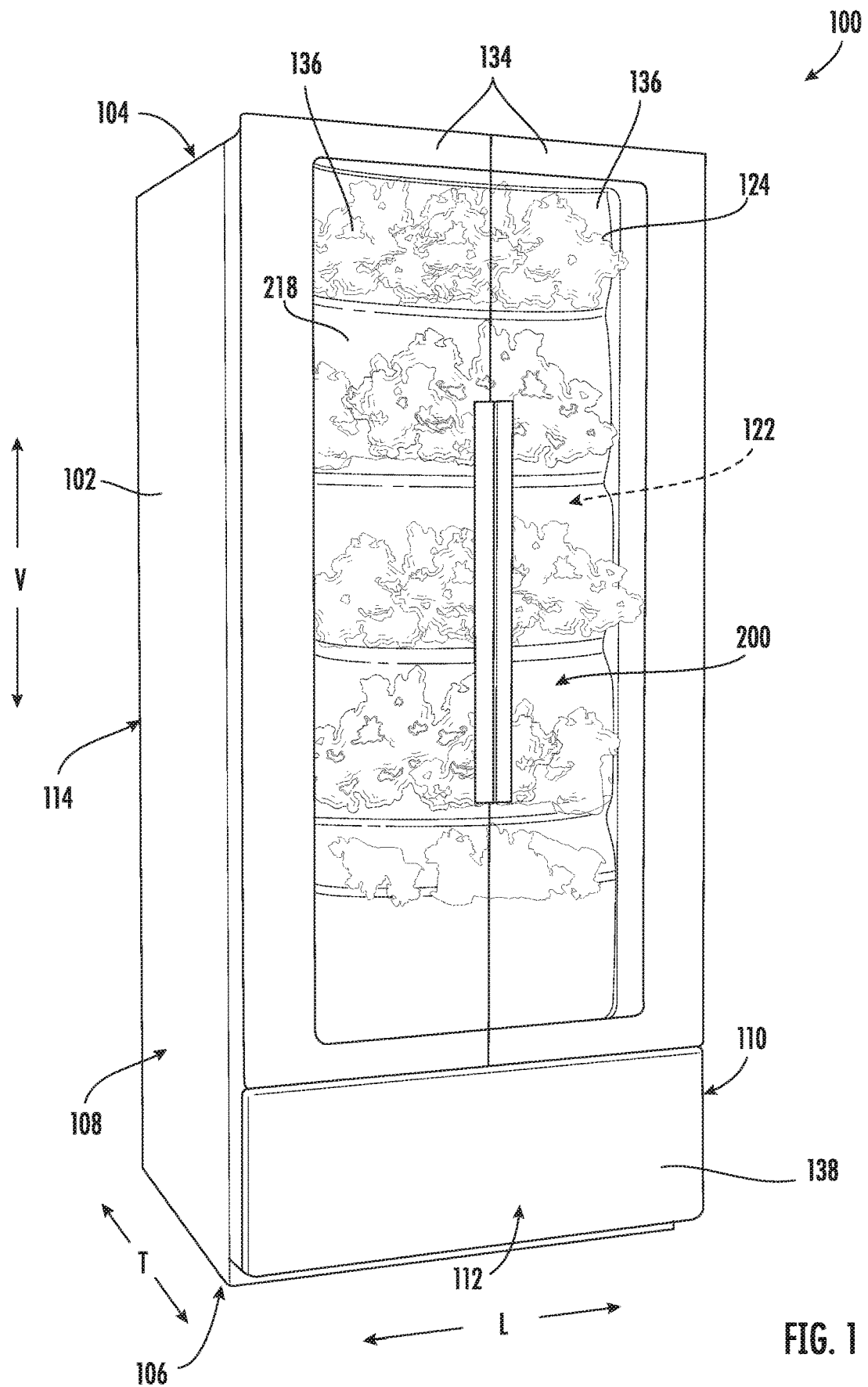
FIG. 1 provides a perspective view of a gardening appliance according to an exemplary embodiment of the present subject matter.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, terms of approximation, such as "approximately," "substantially," or "about," refer to being within a ten percent (10%) margin of error of the stated value. Moreover, as used herein, the terms "first," "second," and "third" may be used interchangeably to distinguish one component from another and are not intended to signify location or importance of the individual components. The terms "upstream" and "downstream" refer to the relative direction with respect to fluid flow in a fluid pathway. For example, "upstream" refers to the direction from which the fluid flows, and "downstream" refers to the direction to which the fluid flows.

FIG. 1 provides a front view of a gardening appliance 100 according to an exemplary embodiment of the present subject matter. According to exemplary embodiments, gardening appliance 100 may be used as an indoor garden center for growing plants. It should be appreciated that the embodiments described herein are intended only for explaining aspects of the present subject matter. Variations and modifications may be made to gardening appliance 100 while remaining within the scope of the present subject matter.

Gardening appliance 100 includes a housing or cabinet 102 that extends between a top 104 and a bottom 106 along a vertical direction V, between a first side 108 and a second side 110 along a lateral direction L, and between a front side 112 and a rear side 114 along a transverse direction T. Each of the vertical direction V, lateral direction L, and transverse direction T are mutually perpendicular to one another and form an orthogonal direction system.

Gardening appliance 100 may include an insulated liner 120 positioned within cabinet 102. Liner 120 may at least partially define a temperature controlled, referred to herein generally as a grow chamber 122, within which plants 124 may be grown. Although gardening appliance 100 is referred to herein as growing plants 124, it should be appreciated that other organisms or living things may be grown or stored in gardening appliance 100. For example, algae, fungi (e.g., including mushrooms), or other living organisms may be grown or stored in gardening appliance 100. The specific application described herein is not intended to limit the scope of the present subject matter.

Cabinet 102, or more specifically, liner 120 may define a substantially enclosed back region or portion 130. In addition, cabinet 102 and liner 120 may define a front opening, referred to herein as front display opening 132, through which a user of gardening appliance 100 may access grow chamber 122, e.g., for harvesting, planting, pruning, or otherwise interacting with plants 124. According to an exemplary embodiment, enclosed back portion 130 may be defined as a portion of liner 120 that defines grow chamber 122 proximate rear side 114 of cabinet 102. In addition, front display opening 132 may generally be positioned proximate or coincide with front side 112 of cabinet 102.

Figure 2:
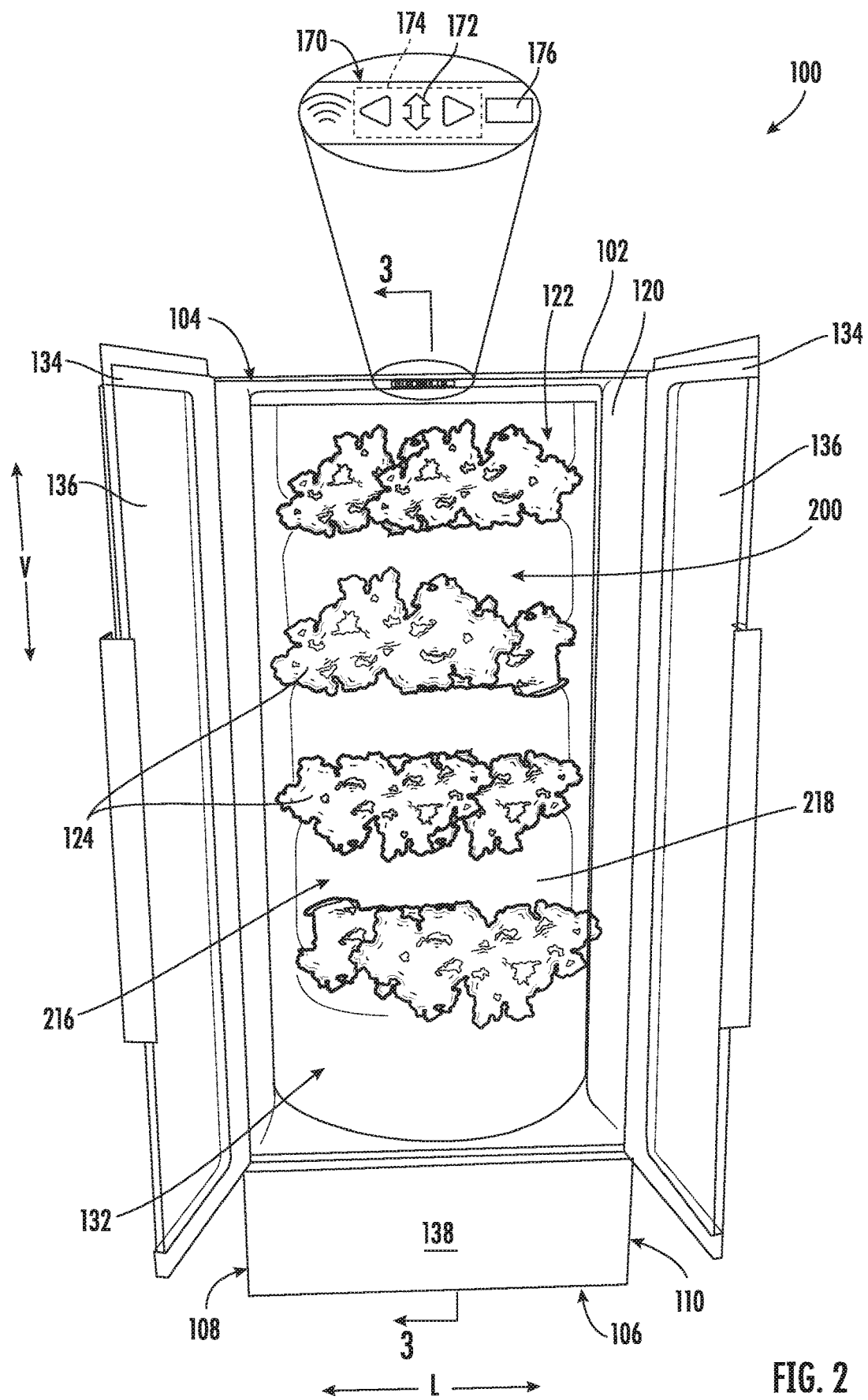
FIG. 2 depicts a front view of the exemplary gardening appliance of FIG. 1 with the doors open according to an exemplary embodiment of the present subject matter.

Gardening appliance 100 may further include one or more doors 134 that are rotatably mounted to cabinet 102 for providing selective access to grow chamber 122. For example, FIG. 1 illustrates doors 134 in the closed position such that they may help insulate grow chamber 122. By contrast, FIG. 2 illustrates doors 134 in the open positioned for accessing grow chamber 122 and plants 124 stored therein. Doors 134 may further include a transparent window 136 through which a user may observe plants 124 without opening doors 134.

Although doors 134 are illustrated as being rectangular and being mounted on front side 112 of cabinet 102 in FIGS. 1 and 2, it should be appreciated that according to alternative embodiments, doors 134 may have different shapes, mounting locations, etc. For example, doors 134 may be curved, may be formed entirely from glass, etc. In addition, doors 134 may have integral features for controlling light passing into and/or out of grow chamber 122, such as internal louvers, tinting, UV treatments, polarization, etc. One skilled in the art will appreciate that other chamber and door configurations are possible and within the scope of the present invention.

According to the illustrated embodiment, cabinet 102 further defines a drawer 138 positioned proximate bottom 106 of cabinet 102 and being slidably mounted to cabinet for providing convenient storage for plant nutrients, system accessories, water filters, etc. In addition, behind drawer 138 is a mechanical compartment 140 for receipt of an environmental control system including a sealed system for regulating the temperature within grow chamber 122, as described in more detail below.

Figure 3:
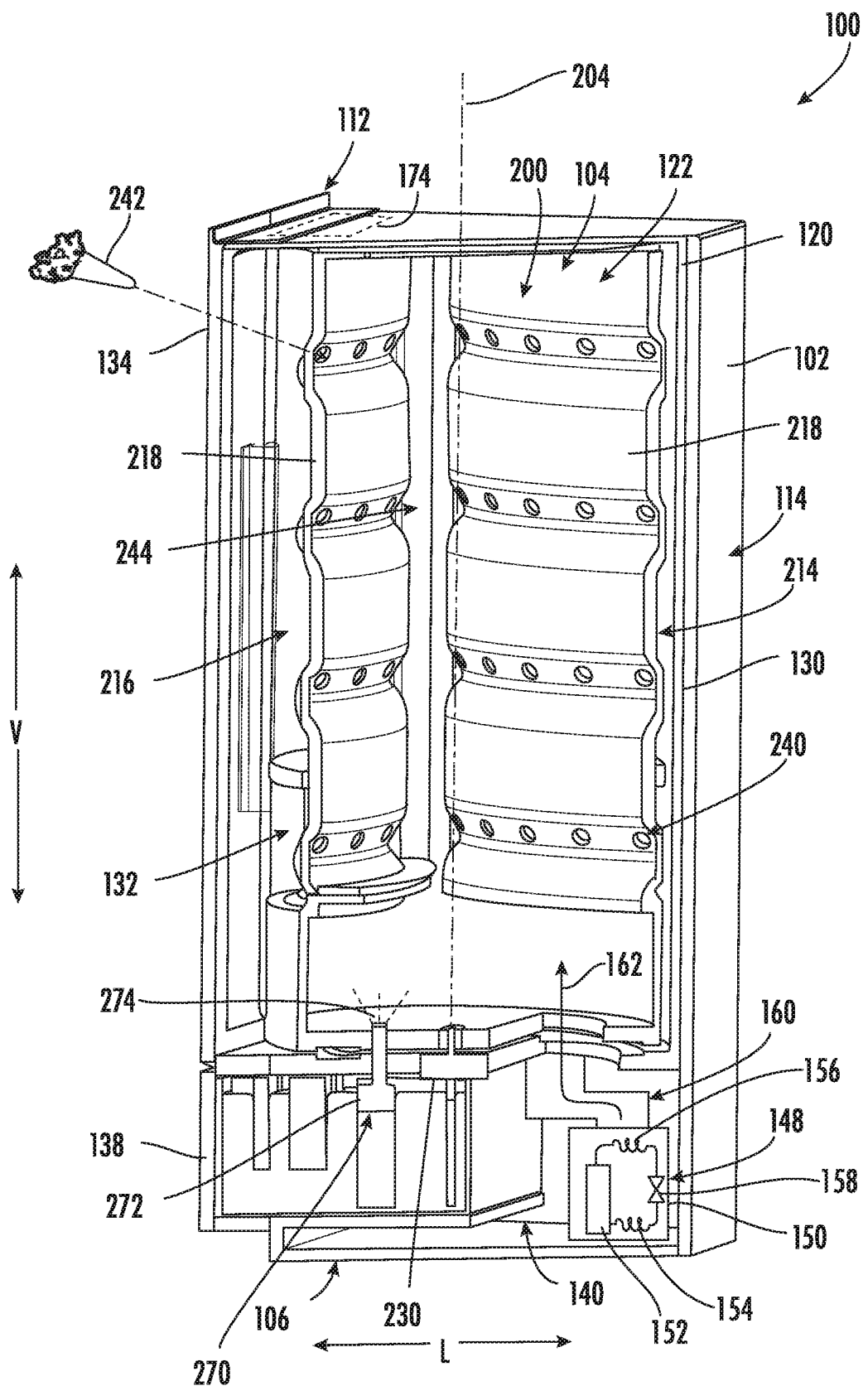
FIG. 3 is a cross sectional view of the exemplary gardening appliance of FIG. 1, taken along Line 3-3 from FIG. 2 with an internal divider removed for clarity.

FIG. 3 provides a schematic view of certain components of an environmental control system 148 that may be used to regulate a temperature within grow chamber 122. Specifically, environmental control system 148 may include a sealed system 150, a duct system 160, and a hydration system 270, or any other suitable components or subsystems for regulating an environment within grow chamber 122, e.g., for facilitating improved or regulated growth of plants 124 positioned therein. Specifically, FIG. 3 illustrates sealed system 150 within mechanical compartment 140. Although an exemplary sealed system is illustrated and described herein, it should be appreciated that variations and modifications may be made to sealed system 150 while remaining within the scope of the present subject matter. For example, sealed system 150 may include additional or alternative components, different ducting configurations, etc.

As shown, sealed system 150 includes a compressor 152, a first heat exchanger or evaporator 154 and a second heat exchanger or condenser 156. As is generally understood, compressor 152 is generally operable to circulate or urge a flow of refrigerant through sealed system 150, which may include various conduits which may be utilized to flow refrigerant between the various components of sealed system 150. Thus, evaporator 154 and condenser 156 may be between and in fluid communication with each other and compressor 152.

During operation of sealed system 150, refrigerant flows from evaporator 154 and to compressor 152, and compressor 152 is generally configured to direct compressed refrigerant from compressor 152 to condenser 156. For example, refrigerant may exit evaporator 154 as a fluid in the form of a superheated vapor. Upon exiting evaporator 154, the refrigerant may enter compressor 152, which is operable to compress the refrigerant. Accordingly, the pressure and temperature of the refrigerant may be increased in compressor 152 such that the refrigerant becomes a more superheated vapor.

Condenser 156 is disposed downstream of compressor 152 and is operable to reject heat from the refrigerant. For example, the superheated vapor from compressor 152 may enter condenser 156 and transfer energy to air surrounding condenser 156 (e.g., to create a flow of heated air). In this manner, the refrigerant condenses into a saturated liquid and/or liquid vapor mixture. A condenser fan (not shown) may be positioned adjacent condenser 156 and may facilitate or urge the flow of heated air across the coils of condenser 156 (e.g., from ambient atmosphere) in order to facilitate heat transfer.

According to the illustrated embodiment, an expansion device or a variable electronic expansion valve 158 may be further provided to regulate refrigerant expansion. During use, variable electronic expansion valve 158 may generally expand the refrigerant, lowering the pressure and temperature thereof. In this regard, refrigerant may exit condenser 156 in the form of high liquid quality/saturated liquid vapor mixture and travel through variable electronic expansion valve 158 before flowing through evaporator 154. Variable electronic expansion valve 158 is generally configured to be adjustable, e.g., such that the flow of refrigerant (e.g., volumetric flow rate in milliliters per second) through variable electronic expansion valve 158 may be selectively varied or adjusted.

Evaporator 154 is disposed downstream of variable electronic expansion valve 158 and is operable to heat refrigerant within evaporator 154, e.g., by absorbing thermal energy from air surrounding the evaporator (e.g., to create a flow of cooled air). For example, the liquid or liquid vapor mixture refrigerant from variable electronic expansion valve 158 may enter evaporator 154. Within evaporator 154, the refrigerant from variable electronic expansion valve 158 receives energy from the flow of cooled air and vaporizes into superheated vapor and/or high quality vapor mixture. An air handler or evaporator fan (not shown) is positioned adjacent evaporator 154 and may facilitate or urge the flow of cooled air across evaporator 154 in order to facilitate heat transfer. From evaporator 154, refrigerant may return to compressor 152 and the vapor-compression cycle may continue.

As explained above, environmental control system 148 includes a sealed system 150 for providing a flow of heated air or a flow cooled air throughout grow chamber 122 as needed. To direct this air, environmental control system 148 includes a duct system 160 for directing the flow of temperature regulated air, identified herein simply as flow of air 162 (see, e.g., FIG. 3). In this regard, for example, an evaporator fan can generate a flow of cooled air as the air passes over evaporator 154 and a condenser fan can generate a flow of heated air as the air passes over condenser 156.

These flows of air 162 are routed through a cooled air supply duct and/or a heated air supply duct (not shown), respectively. In this regard, it should be appreciated that environmental control system 148 may generally include a plurality of ducts, dampers, diverter assemblies, and/or air handlers to facilitate operation in a cooling mode, in a heating mode, in both a heating and cooling mode, or any other mode suitable for regulating the environment within grow chamber 122. It should be appreciated that duct system 160 may vary in complexity and may regulate the flows of air from sealed system 150 in any suitable arrangement through any suitable portion of grow chamber 122.

Gardening appliance 100 may include a control panel 170. Control panel 170 includes one or more input selectors 172, such as e.g., knobs, buttons, push buttons, touchscreen interfaces, etc. In addition, input selectors 172 may be used to specify or set various settings of gardening appliance 100, such as e.g., settings associated with operation of sealed system 150. Input selectors 172 may be in communication with a processing device or controller 174. Control signals generated in or by controller 174 operate gardening appliance 100 in response to input selectors 172. Additionally, control panel 170 may include a display 176, such as an indicator light or a screen. Display 176 is communicatively coupled with controller 174 and may display information in response to signals from controller 174. Further, as will be described herein, controller 174 may be communicatively coupled with other components of gardening appliance 100, such as e.g., one or more sensors, motors, or other components.

As used herein, "processing device" or "controller" may refer to one or more microprocessors or semiconductor devices and is not restricted necessarily to a single element. The processing device can be programmed to operate gardening appliance 100. The processing device may include, or be associated with, one or more memory elements (e.g., non-transitory storage media). In some such embodiments, the memory elements include electrically erasable, programmable read only memory (EEPROM). Generally, the memory elements can store information accessible processing device, including instructions that can be executed by processing device. Optionally, the instructions can be software or any set of instructions and/or data that when executed by the processing device, cause the processing device to perform operations.

Referring now generally to FIGS. 1 through 8, gardening appliance 100 generally includes a rotatable carousel, referred to herein as a grow module 200 that is mounted within liner 120, e.g., such that it is within grow chamber 122. As illustrated, grow module 200 includes a central hub 202 that extends along and is rotatable about a central axis 204. Specifically, according to the illustrated embodiment, central axis 204 is parallel to the vertical direction V. However, it should be appreciated that central axis 204 could alternatively extend in any suitable direction, e.g., such as the horizontal direction. In this regard, grow module 200 generally defines an axial direction, i.e., parallel to central axis 204, a radial direction R that extends perpendicular to central axis 204, and a circumferential direction C that extends around central axis 204 (e.g. in a plane perpendicular to central axis 204).

Grow module 200 may further include a plurality of partitions 206 that extend from central hub 202 substantially along the radial direction R. In this manner, grow module 200 defines a plurality of chambers, referred to herein generally by reference numeral 210, by dividing or partitioning grow chamber 122. Referring specifically to a first embodiment of grow module 200 illustrated in FIGS. 1 through 8, grow module 200 includes three partitions 206 to define a first chamber 212, a second chamber 214, and a third chamber 216, which are circumferentially spaced relative to each other. In general, as grow module 200 is rotated within grow chamber 122, the plurality of chambers 210 define substantially separate and distinct growing environments, e.g., for growing plants 124 having different growth needs.

More specifically, partitions 206 may extend from central hub 202 to a location immediately adjacent liner 120. Although partitions 206 are described as extending along the radial direction, it should be appreciated that they need not be entirely radially extending. For example, according to the illustrated embodiment, the distal ends of each partition is joined with an adjacent partition using an arcuate wall 218, which is generally used to support plants 124.

Notably, it is desirable according to exemplary embodiments to form a substantial seal between partitions 206 and liner 120. Therefore, according to an exemplary embodiment, grow module 200 may define a grow module diameter 220 (e.g., defined by its substantially circular footprint formed in a horizontal plane). Similarly, enclosed back portion 130 of liner 120 may be substantially cylindrical and may define a liner diameter 222. In order to prevent a significant amount of air from escaping between partitions 206 and liner 120, liner diameter 222 may be substantially equal to or slightly larger than grow module diameter 220.

According to still other embodiments, grow module 200 may include one or more sealing elements 224 positioned on a radially distal end of each of partitions 206. In this regard, sealing elements 224 may extend from partitions 206 toward liner 120 to contact and seal against liner 120. For example, according to the illustrated embodiment, sealing elements 224 are wiper blades formed from silicone or another suitably resilient material. Thus, as grow module 200 rotates, sealing elements 224 slide against liner 120 to substantially seal each of the plurality of chambers 210. It should be appreciated that as used herein, the term "substantial seal" and the like is not intended to refer to a perfectly airtight junction. Instead, this term is generally used to refer to an environment which may be regulated independently of adjacent environments to a reasonable degree. For example, if plants 124 and the first chamber 212 prefer a 10° F. increase in temperature relative to plants 124 and second chamber 214, the substantial seal between these two chambers may facilitate such temperature difference.

Referring now specifically to FIG. 3, gardening appliance 100 may further include a motor 230 or another suitable driving element or device for selectively rotating grow module 200 during operation of gardening appliance 100. In this regard, according to the illustrated embodiment, motor 230 is positioned below grow module 200, e.g., within mechanical compartment 140, and is operably coupled to grow module 200 along central axis 204 for rotating grow module 200.

As used herein, "motor" may refer to any suitable drive motor and/or transmission assembly for rotating grow module 200. For example, motor 230 may be a brushless DC electric motor, a stepper motor, or any other suitable type or configuration of motor. For example, motor 230 may be an AC motor, an induction motor, a permanent magnet synchronous motor, or any other suitable type of AC motor. In addition, motor 230 may include any suitable transmission assemblies, clutch mechanisms, or other components.

According to an exemplary embodiment, motor 230 may be operably coupled to controller 174, which is programmed to rotate grow module 200 according to predetermined operating cycles, based on user inputs (e.g. via touch buttons 172), etc. In addition, controller 174 may be communicatively coupled to one or more sensors, such as temperature or humidity sensors, positioned within the various chambers 210 for measuring temperatures and/or humidity, respectively. Controller 174 may then operate motor 230 in order to maintain desired environmental conditions for each of the respective chambers 210. For example, as will be described in more detail below, gardening appliance 100 includes features for providing certain locations of gardening appliance 100 with light, temperature control, proper moisture, nutrients, and other requirements for suitable plant growth. Motor 230 may be used to position specific chambers 210 where needed to receive such growth requirements.

According to an exemplary embodiment, such as where three partitions 206 form three chambers 212-216, controller 174 may operate motor 230 to index grow module 200 sequentially through a number of preselected positions. More specifically, motor 230 may rotate grow module 200 in a counterclockwise direction (e.g. when viewed from a top of grow module 200) in 120° increments to move chambers 210 between sealed positions and display positions. As used herein, a chamber 210 is considered to be in a "sealed position" when that chamber 210 is substantially sealed between grow module 200 (i.e., central hub 202 and adjacent partitions 206) and liner 120. By contrast, a chamber 210 is considered to be in a "display position" when that chamber 210 is at least partially exposed to front display opening 132, such that a user may access plants 124 positioned within that chamber 210.

Figure 4:
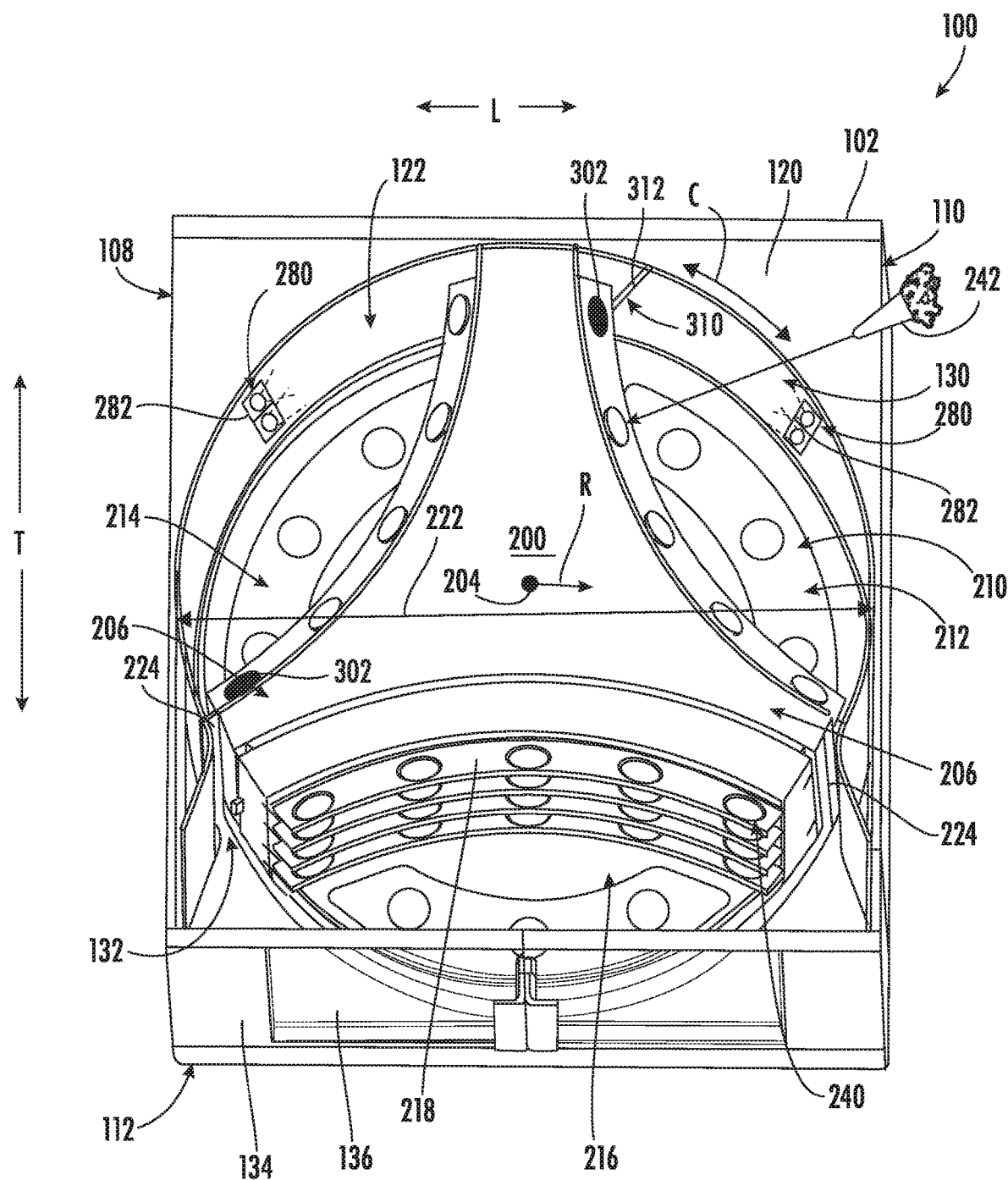
FIG. 4 is a top perspective view of the exemplary gardening appliance of FIG. 1, with the top panel of the cabinet removed to reveal a rotatable grow module according to an exemplary embodiment of the present subject matter.
Figure 5:
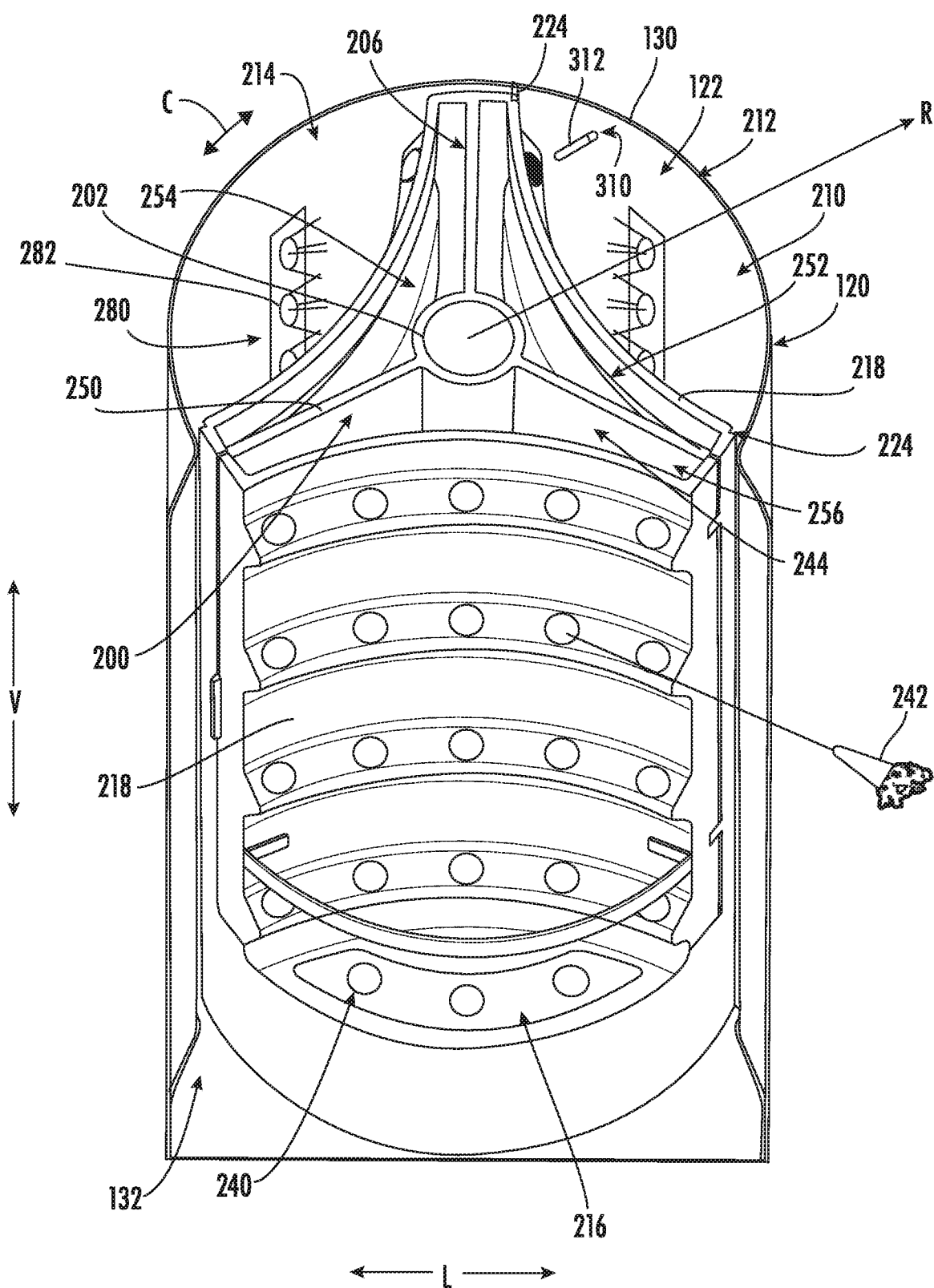
FIG. 5 provides a perspective cross sectional view of the exemplary gardening appliance of FIG. 1 according to another exemplary embodiment of the present subject matter.
Figure 6:
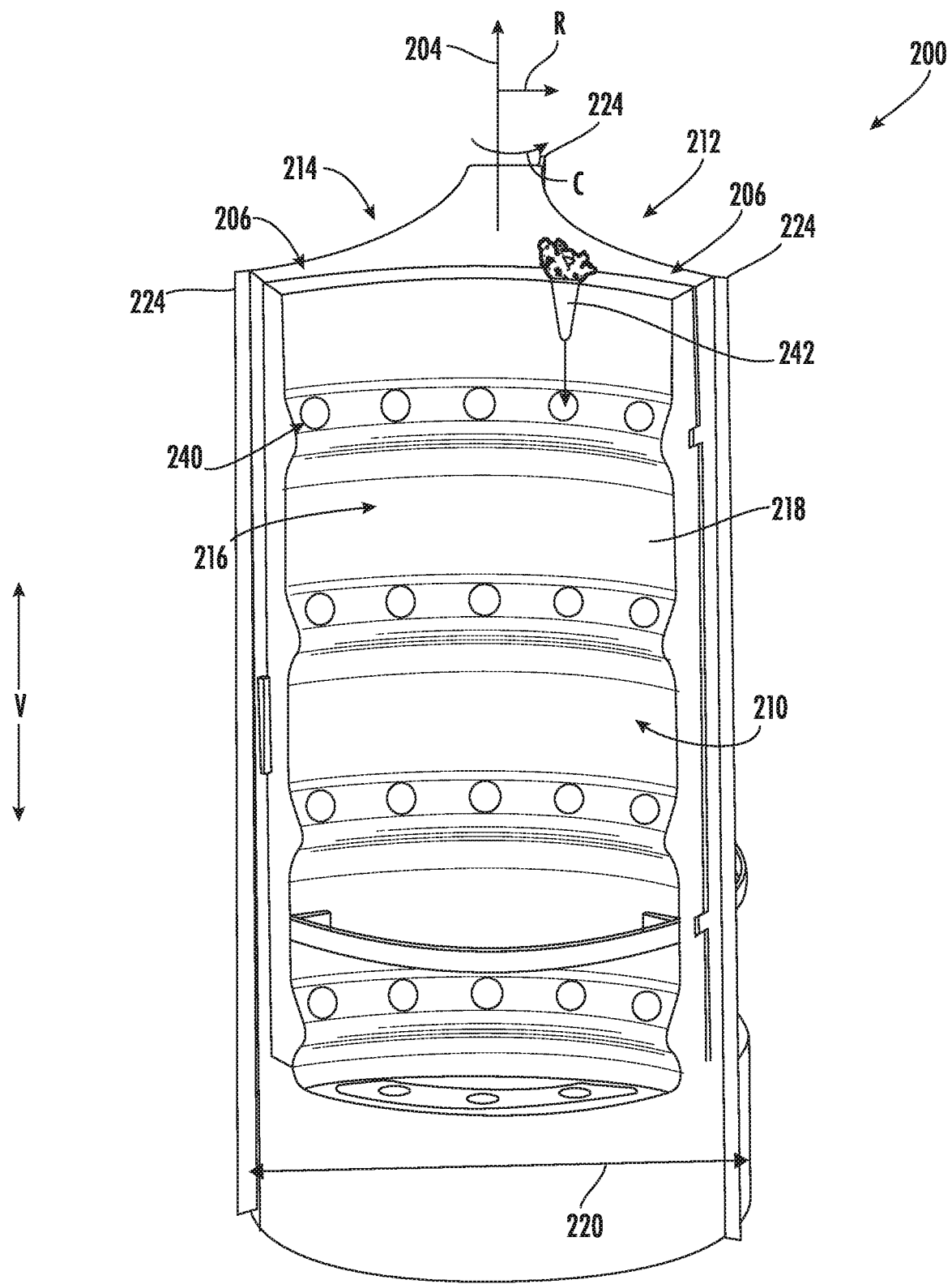
FIG. 6 provides a perspective view of the grow module of the exemplary gardening appliance of FIG. 1 according to another exemplary embodiment of the present subject matter.

For example, as illustrated in FIGS. 4 and 5, first chamber 212 and second chamber 214 are both in a sealed position, whereas third chamber 216 is in a display position. As motor 230 rotates grow module 200 by 120 degrees in the counterclockwise direction, second chamber 214 will enter the display position, while first chamber 212 and third chamber 216 will be in the sealed positions. Motor 230 may continue to rotate grow module 200 in such increments to cycle grow chambers 210 between these sealed and display positions.

Referring now generally to FIGS. 4 through 8, grow module 200 will be described in more detail according to an exemplary embodiment of the present subject matter. As shown, grow module 200 defines a plurality of apertures 240 which are generally configured for receiving plant pods 242 into an internal root chamber 244. Plant pods 242 generally contain seedlings or other material for growing plants positioned within a mesh or other support structure through which roots of plants 124 may grow within grow module 200. A user may insert a portion of plant pod 242 (e.g., a seed end or root end 246) having the desired seeds through one of the plurality of apertures 240 into root chamber 244. A plant end 248 of the plant pod 242 may remain within grow chamber 210 such that plants 124 may grow from grow module 200 such that they are accessible by a user. In this regard, grow module 200 defines root chamber 244, e.g., within at least one of central hub 202 and the plurality of partitions 206. As will be explained below, water and other nutrients may be supplied to the root end 246 of plant pods 242 within root chamber 244. Notably, apertures 240 may be covered by a flat flapper seal (not shown) to prevent water from escaping root chamber 244 when no plant pod 242 is installed.

Figure 7:
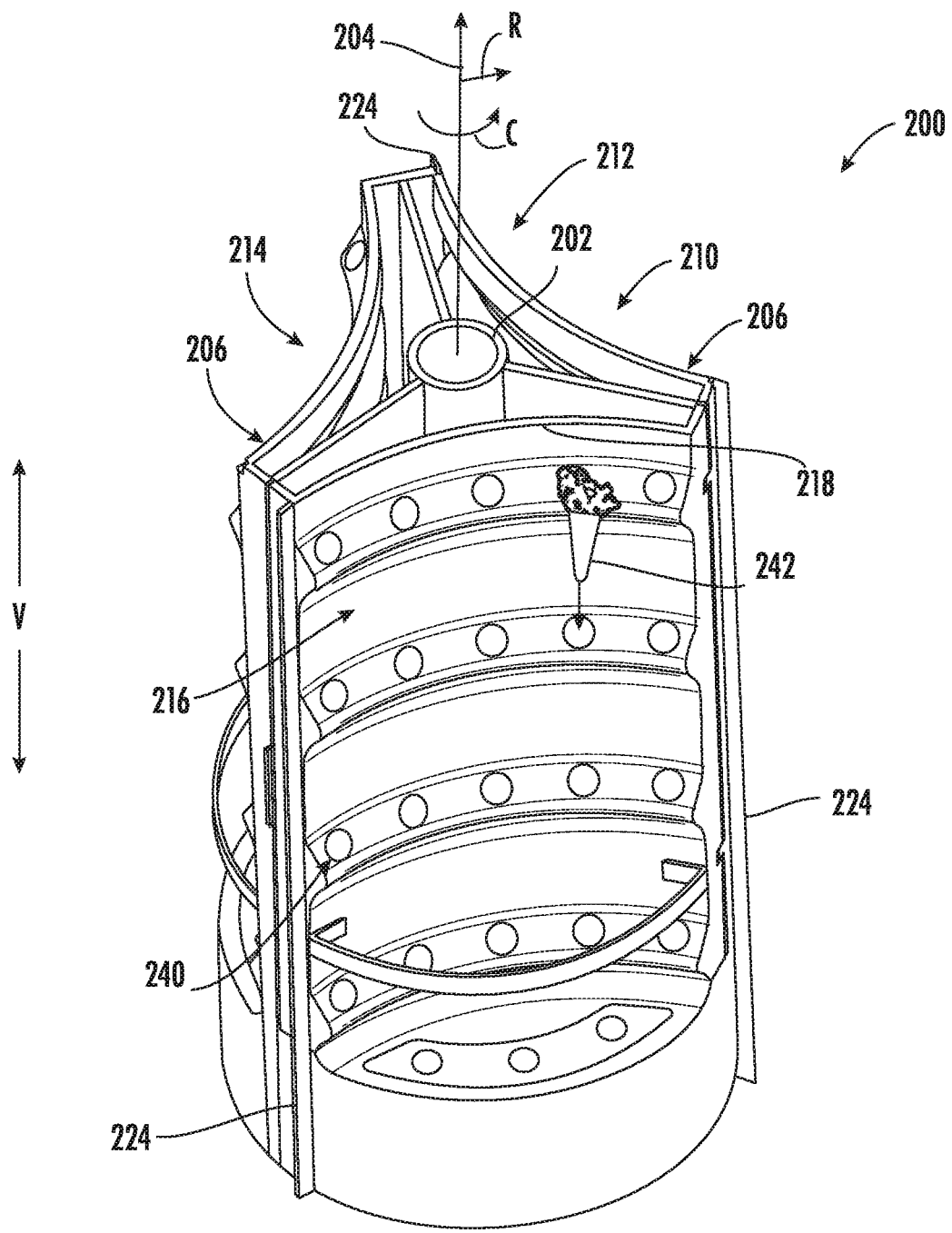
FIG. 7 provides a perspective cross sectional view of the exemplary grow module of FIG. 6 according to another exemplary embodiment of the present subject matter.
Figure 8:
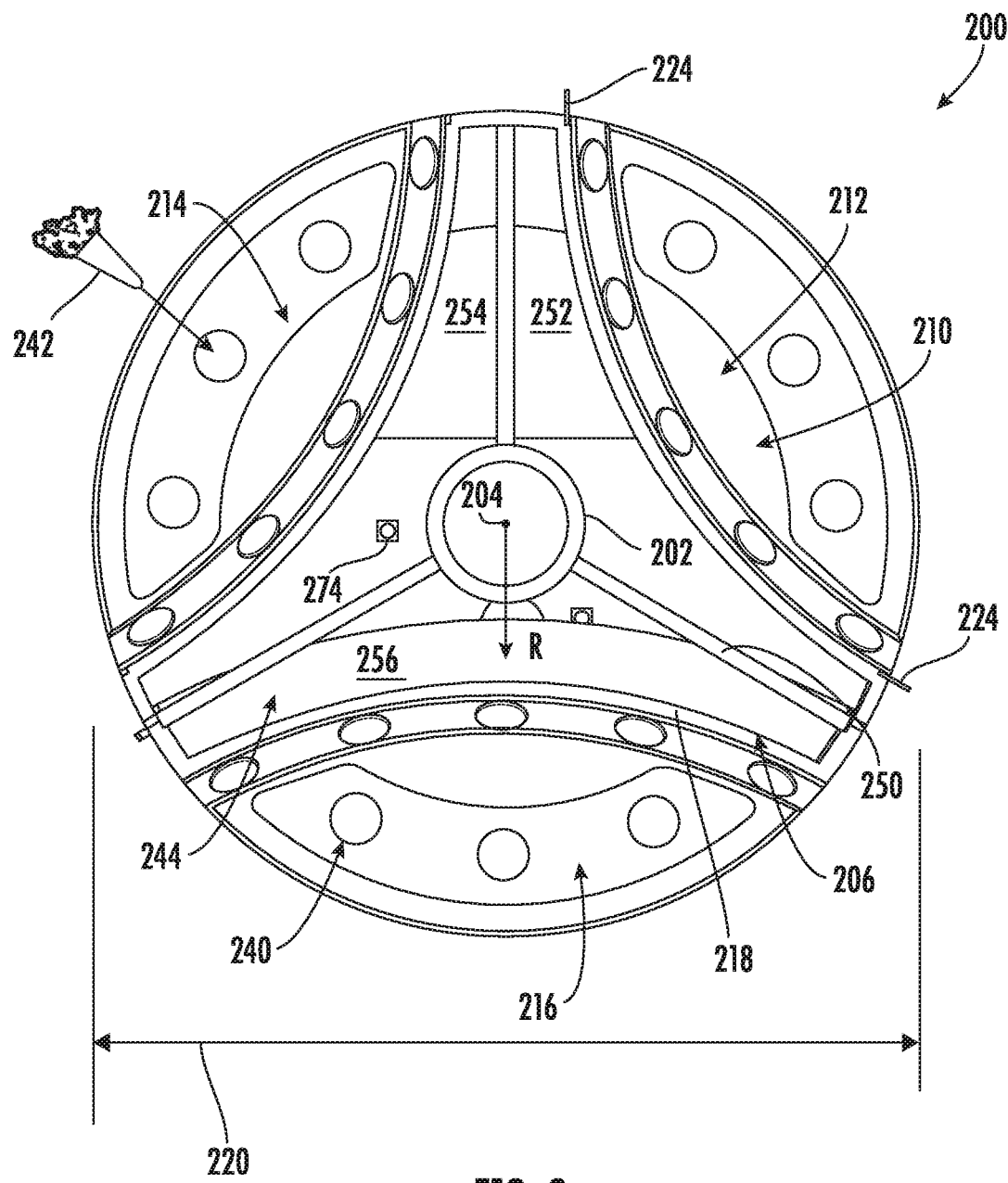
FIG. 8 provides a top cross-sectional view of the exemplary grow module of FIG. 6 according to another exemplary embodiment of the present subject matter.

As best shown in FIGS. 5 and 7, grow module 200 may further include an internal divider 250 that is positioned within root chamber 244 to divide root chamber 244 into a plurality of root chambers, each of the plurality of root chambers being in fluid communication with one of the plurality of grow chambers 210 through the plurality of apertures 240. More specifically, according to the illustrated embodiment, internal divider 250 may divide root chamber 244 into a first root chamber 252, a second root chamber 254, and a third root chamber 256. According to an exemplary embodiment, first root chamber 252 may provide water and nutrients to plants 124 positioned in the first grow chamber 212, second root chamber 254 may provide water and nutrients to plants 124 positioned in the second grow chamber 214, and third root chamber 256 may provide water and nutrients to plants 124 positioned in the third grow chamber 216. In this manner, environmental control system 148 may control the temperature and/or humidity of each of the plurality of chambers 212-216 and the plurality of root chambers 252-256 independently of each other.

Environmental control system 148 may further include a hydration system 270 which is generally configured for providing water to plants 124 to support their growth. Specifically, according to the illustrated embodiment, hydration system 270 generally includes a water supply 272 and misting device 274 (e.g., such as a fine mist spray nozzle or nozzles). For example, water supply 272 may be a reservoir containing water (e.g., distilled water) or may be a direct connection municipal water supply. Misting device 274 may be positioned at a bottom of root chamber 244 and may be configured for charging root chamber 244 with mist for hydrating the roots of plants 124. Alternatively, misting devices 274 may pass through central hub 204 along the vertical direction V and periodically include a nozzle for spraying a mist or water into root chamber 244. Because various plants 124 may require different amounts of water for desired growth, hydration system 270 may alternatively include a plurality of misting devices 274, e.g., all coupled to water supply 272, but being selectively operated to charge each of first root chamber 252, second root chamber 254, and third root chamber 256 independently of each other.

Notably, environmental control system 148 described above is generally configured for regulating the temperature and humidity (e.g., or some other suitable water level quantity or measurement) within one or all of the plurality of chambers 210 and/or root chambers 252-256 independently of each other. In this manner, a versatile and desirable growing environment may be obtained for each and every chamber 210.

Referring now for example to FIGS. 4 and 5, gardening appliance 100 may further include a light assembly 280 which is generally configured for providing light into selected grow chambers 210 to facilitate photosynthesis and growth of plants 124. As shown, light assembly 280 may include a plurality of light sources 282 stacked in an array, e.g., extending along the vertical direction V. For example, light sources 282 may be mounted directly to liner 120 within grow chamber 122, or may alternatively be positioned behind liner 120 such that light is projected through a transparent window or light pipe into grow chamber 122. The position, configuration, and type of light sources 282 described herein are not intended to limit the scope of the present subject matter in any manner.

Light sources 282 may be provided as any suitable number, type, position, and configuration of electrical light source(s), using any suitable light technology and illuminating in any suitable color. For example, according to the illustrated embodiment, light source 282 includes one or more light emitting diodes (LEDs), which may each illuminate in a single color (e.g., white LEDs), or which may each illuminate in multiple colors (e.g., multi-color or RGB LEDs) depending on the control signal from controller 174. However, it should be appreciated that according to alternative embodiments, light sources 282 may include any other suitable traditional light bulbs or sources, such as halogen bulbs, fluorescent bulbs, incandescent bulbs, glow bars, a fiber light source, etc.

As explained above, light generated from light assembly 280 may result in light pollution within a room where gardening appliance 100 is located. Therefore, aspects of the present subject matter are directed to features for reducing light pollution, or to the blocking of light from light sources 282 through front display opening 132. Specifically, as illustrated, light assembly 280 is positioned only within the enclosed back portion 130 of liner 120 such that only grow chambers 210 which are in a sealed position are exposed to light from light sources 282. Specifically, grow module 200 acts as a physical partition between light assemblies 280 and front display opening 132. In this manner, as illustrated in FIG. 5, no light may pass from first chamber 212 or second chamber 214 through grow module 200 and out front display opening 132. As grow module 200 rotates, two of the three grow chambers 210 will receive light from light assembly 280 at a time. According still other embodiments, a single light assembly may be used to reduce costs, whereby only a single grow chamber 210 will be lit at a single time.

Gardening appliance 100 and grow module 200 have been described above to explain an exemplary embodiment of the present subject matter. However, it should be appreciated that variations and modifications may be made while remaining within the scope of the present subject matter. For example, according to alternative embodiments, gardening appliance 100 may be a simplified to a two-chamber embodiment with a square liner 120 and a grow module 200 having two partitions 206 extending from opposite sides of central hub 202 to define a first grow chamber and a second grow chamber. According to such an embodiment, by rotating grow module 200 by 180 degrees about central axis 206, the first chamber may alternate between the sealed position (e.g., facing rear side 114 of cabinet 102) and the display position (e.g., facing front side 112 of cabinet 102). By contrast, the same rotation will move the second chamber from the display position to the sealed position.

According to still other embodiments, gardening appliance 100 may include a three chamber grow module 200 but may have a modified cabinet 102 such that front display opening 132 is wider and two of the three grow chambers 210 are displayed at a single time. Thus, first chamber 212 may be in the sealed position, while second chamber 214 and third chamber 216 may be in the display positions. As grow module 200 is rotated counterclockwise, first chamber 212 is moved into the display position and third chamber 216 is moved into the sealed position.

Figure 9:
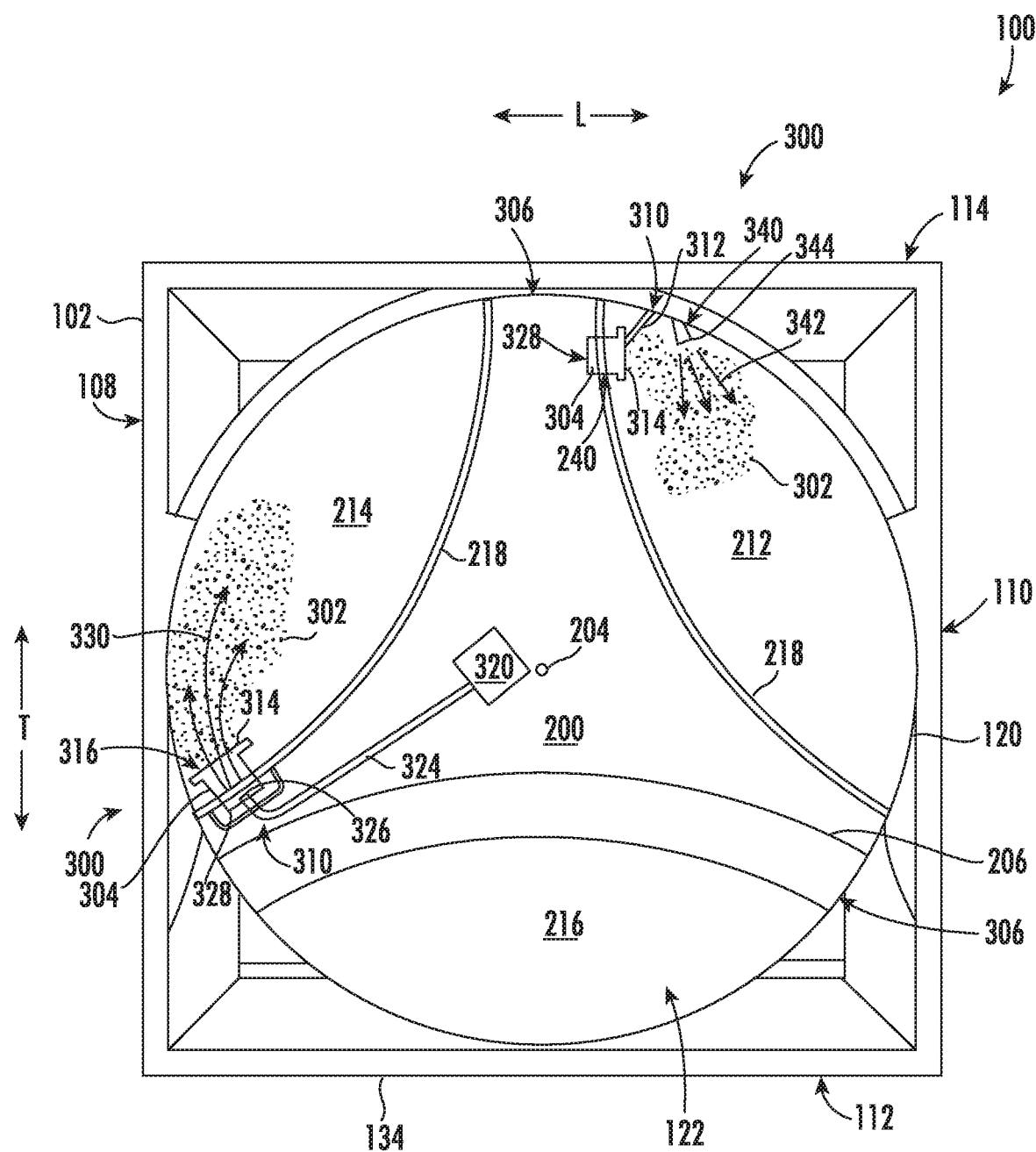
FIG. 9 provides a top, schematic view of a grow module and a pollen distribution system of the exemplary gardening appliance of FIG. 1 according to an exemplary embodiment of the present subject matter.
Figure 10:
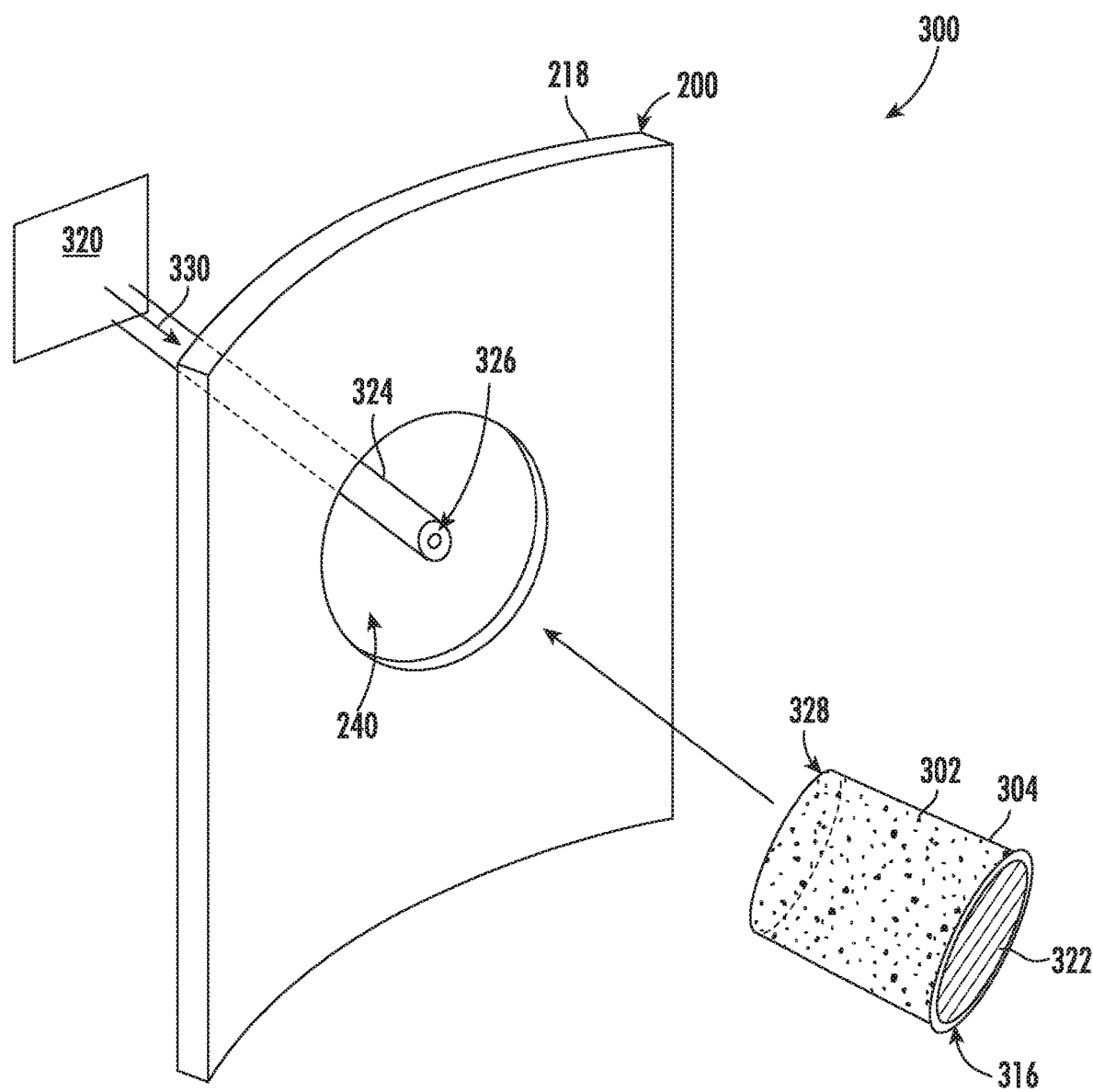
FIG. 10 provides a schematic view of a pollen ejection device of the exemplary pollen distribution system of FIG. 9 according to an exemplary embodiment of the present subject matter.

Referring now specifically to FIGS. 9 and 10, gardening appliance 100 may further include a pollen distribution system 300 that is generally configured for distributing pollen throughout one or more chambers 210 of gardening appliance 100. In this regard, for example, pollen distribution system 300 may be integrated into gardening appliance 100 for automatically discharging, dispersing, and/or directing pollen (e.g., identified herein generally by reference numeral 302) to desired locations or toward desired plants 124 within grow chamber 122. Specifically, pollen 302 is described herein is being stored in one or more pollen pods 304 which are selectively discharged by pollen distribution system 300. Although an exemplary pollen distribution system 300 is described herein, it should be appreciated that variations and modifications may be made to system 300 while remaining within the scope of the present subject matter.

As used herein, the term "pollen" is generally intended to refer to the powdery or granular substance used for facilitating the germination and growth of plants 124. In general, pollen 302 may have any suitable type, quantity, and grain size. In addition, although pollen pods 304 are described herein is containing pollen 302, it should be appreciated that according to alternative embodiments, any other suitable substance for facilitating improved growth of plants 124 may be contained within pollen pods 304. Indeed, aspects of the present subject matter may be used in alternative embodiments for discharging or directing any suitable substance, fluid, chemicals, or other compositions throughout chambers 210 or elsewhere within gardening appliance 100.

According to the illustrated embodiment, each pollen pod 304 may be mounted on or within grow module 200, e.g., such that it may rotate with grow module 200. Specifically, as best shown in FIG. 10, pollen pods 304 may be received in one of apertures 240 that are defined through arcuate wall 218. Thus, according to an exemplary embodiment, pollen pods 304 may have substantially similar size, shape, and cross-sectional geometry as plant pods 242. However, it should be appreciated that according to alternative embodiments, pollen pods 304 may have a unique shape configured for receipt within a complementary recess or aperture defined in grow module 200. In this regard, for example, arcuate wall 218 may define one or more dedicated pollen pod apertures 240 having a unique shape and size corresponding to pollen pods 204.

In addition, it should be appreciated that pollen pods 304 may be positioned at any suitable location within gardening appliance 100. For example, according to the illustrated embodiment, pollen pods 304 may be positioned toward a top of grow module 200, e.g., proximate top 104 of cabinet 102. In this manner, when pollen 302 is discharged from pollen pods 304, it may fall under the force of gravity to plants 124 positioned below pollen pods 304. In addition, pollen pods 304 may be positioned proximate a distal end 306 of partitions 206, e.g., proximate liner 120, so that pollen pods 304 may be easily accessed and discharged as grow module 200 rotates, as described in more detail below. According still other embodiments, pollen pods 304 may be received in any other suitable location within each chamber 210. For example, a unique pollen pod 304 may be configured for receipt in unique locations adjacent corresponding plants 124. It should be appreciated that any suitable position, orientation, or size of pollen pods 304 may be used while remaining within the scope of the present subject matter.

Referring still to FIGS. 9 and 10, pollen distribution system 300 may further include a pollen ejection device 310 which is generally configured for contacting, puncturing, or otherwise engaging pollen pods 304 in a manner that initiates the distribution of pollen 302. Specifically, as illustrated for example in first chamber 212 in FIG. 9, pollen ejection device 310 includes a protruding member 312 that is positioned at a fixed location on liner 120 and extends inwards along the radial direction R toward grow module 200. In addition, pollen pods 304 may define a removable or puncturable cover 314 that is positioned on an open end 316 of pollen pod 304 for containing pollen 302 therein.

In this manner, as grow module 200 rotates pollen pods 304 past protruding member 312, protruding member 312 may puncture, tear, or otherwise remove cover 314 such that pollen 302 is no longer contained within pollen pods 304. Although protruding member 312 as illustrated as a puncturing device, it should be appreciated that according to alternative embodiments, protruding member 312 could be any other feature that protrudes from liner 120 for engaging pollen pods 304, such as one or more ribs, bumps, surface aberrations, or other protruding features.

In addition to having a protruding member 312 for puncturing or opening pollen pods 304, pollen distribution system 300 may include features for discharging, dispersing, or distributing pollen 302 after it leaves pollen pod 304. For example, according to an exemplary embodiment, pollen pod 304 may be pressurized such that puncturing removable cover 314 causes pollen 302 to be immediately ejected into grow chamber 122.

Notably, the pollen ejection device 310 illustrated in first chamber 212 engages pollen pod 304 to discharge pollen 302 when grow module 200 rotates pollen pods 304 past a predetermined angular position where pollen ejection device 310 is mounted. However, it should be appreciated that according to alternative embodiments, other means for ejecting pollen 302 at any other suitable location may be used while remaining within the scope of the present subject matter. In this regard, as shown for example in second chamber 214 of FIG. 9 and illustrated schematically in FIG. 10, pollen distribution system 300 may include a source of compressed or pressurized air 320 that selectively ejects pollen 302 from a pollen pod 304.

In this regard, as best illustrated in FIG. 10, pollen pods 304 may include a permeable wall 322 positioned over open end 316 of pollen pod 304. In this regard, permeable wall 322 may generally be made from a mesh having a fine enough mesh size to generally contain pollen 302. According to an exemplary embodiment, protruding member 312 punctures pollen pod 304 before pressurized air supply 320 discharges pollen 302. According to the illustrated embodiment, pressurized air supply 320 may be in fluid communication with pollen pod 304 through an air supply conduit 324. Specifically, as illustrated, air supply conduit 324 terminates in a puncturing nozzle 326 that may penetrate a bottom end 328 of pollen pod 304 when it is inserted into pollen pod aperture 240 of grow module 200.

According to an exemplary embodiment, pollen 302 may be contained within pollen pods 304 even after being punctured by air supply conduit 324. However, when pollination is desired, pressurized air supply 320 may discharge a flow of air 330 that passes through air supply conduit 324 into pollen pod 304 and discharges the air and pollen 302 through permeable cover 322 and out of open end 316. Although air supply conduit 324 is illustrated as puncturing pollen pod 304 and permeable wall 322 is illustrated as substantially containing pollen 302, it should be appreciated that aspects of the present subject matter may be used to discharge pollen 302 in any other suitable manner. For example, according to an alternative embodiment, protruding member 312 may be coupled to pressurized air supply and may be constructed similar to air supply conduit for both puncturing pollen pod 304 and providing the flow of air 330 to discharge pollen 302.

For example, according to an alternative embodiment, a non-permeable removable cover 314 may be positioned on pollen pod 304 and may be designed to fail or rupture at a predetermined pressure. In this manner, pressurized air supply 320 may build up pressure within pollen pod 304 until the failure threshold of removable cover 314 is reached, at which time cover 314 will rupture and pollen pods 304 will rapidly discharge to spread pollen 302 throughout grow chamber 122. Other configurations and discharge mechanisms are possible and within the scope of the present subject matter.

According to still other embodiments, gardening appliance 100 may include additional features for facilitating the ejection and dispersion of pollen 302. For example, according to certain exemplary embodiments, motor 230 may be configured for rotating grow module 200 in a manner that agitates pollen pods 304 to discharge pollen 302. Specifically, for example, removable cover 314 may be removed altogether from pollen pod 304, which may be set up right (e.g., open end 316 up) for containing pollen 302. When pollen dispersion is desired, motor 230 may selectively oscillate to agitate pollen pod 304 and cause a portion of pollen 302 to eject from pollen pod 304.

Referring still to FIG. 9, pollen distribution system 300 may additionally include an auxiliary air circulation device 340 which is generally configured for discharging a flow of auxiliary air 342 in the desired direction and at the desired flow rate to disperse pollen 302 after it is ejected from pollen pods 304. For example, according to the illustrated embodiment, auxiliary air circulation device 340 comprises a nozzle 344 positioned downstream of pollen ejection device 310 relative to the direction of rotation of grow module 200. Thus, as soon as pollen ejection device 310 causes pollen pod 304 to discharge, auxiliary air circulation device 340 may urge a flow of auxiliary air 342 in the direction of preferred pollen distribution. In this manner, auxiliary air 342 may pick up and entrain pollen 302 and distribute the pollen 302 to the desired plants 124.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A gardening appliance, comprising:

a liner positioned within a cabinet and defining a grow chamber;

a grow module mounted within the liner, the grow module comprising a central hub rotatable about an axis and a plurality of partitions extending from the central hub substantially along a radial direction to define a plurality of grow chambers spaced apart along a circumferential direction;

an aperture defined in the grow module for receiving a pollen pod containing pollen; and a pollen ejection device comprising a protruding member configured for puncturing the pollen pod to release a portion of the pollen.

2. The gardening appliance of claim 1, further comprising the pollen pod comprising a removable cover positioned over an opening of the pollen pod, wherein the pollen ejection device is configured for puncturing or removing the removable cover to release the pollen.

3. The gardening appliance of claim 1, further comprising the pollen pod, wherein the pollen pod is pressurized, and wherein the pollen ejection device is a puncturing device for breaking the pollen pod to release the pollen.

4. The gardening appliance of claim 1, further comprising the pollen pod comprising a permeable wall, and wherein the pollen ejection device comprises a source of compressed air to eject the pollen through the permeable wall.

5. The gardening appliance of claim 1, further comprising the pollen pod, wherein the pollen ejection device engages the pollen pod when the grow module rotates past a predetermined angular position.

6. The gardening appliance of claim 1, further comprising the pollen pod, wherein the pollen pods are positioned proximate a distal end of the grow module proximate the liner, and wherein the pollen ejection device punctures the pollen pod as it rotates past the protruding member.

7. The gardening appliance of claim 1, wherein the protruding member comprising at least one of ribs, bumps, surface aberrations, or a puncturing member.

8. The gardening appliance of claim 1, further comprising:

a motor mechanically coupled to the grow module for selectively rotating the grow module, wherein the motor selectively oscillates that grow module to discharge the pollen.

9. The gardening appliance of claim 1, further comprising the pollen pod, wherein the aperture is one of a plurality of apertures defined through the grow module, the plurality of apertures being configured for receiving a plurality of plant pods that grow a plurality of plants, wherein the pollen pod is positioned in one of the plurality of apertures.

10. The gardening appliance of claim 9, further comprising the pollen pod, wherein one of the plurality of apertures is a pollen pod aperture, wherein the pollen pod is uniquely shaped for fitting into the pollen pod aperture.

11. The gardening appliance of claim 9, further comprising the pollen pod, wherein the pollen pod is the same size as a plant pod also configured for receipt in one of the plurality of apertures.

12. The gardening appliance of claim 1, further comprising the pollen pod, wherein the pollen pod is positioned toward a top of the grow module.

13. The gardening appliance of claim 1, further comprising:

the pollen pod; and an auxiliary air circulation device for circulating the pollen after the pollen is discharged from the pollen pod.

14. A gardening appliance, the gardening appliance comprising: a liner defining a grow chamber; a grow module rotatably mounted within the grow chamber and defining an aperture for receiving a pollen pod containing pollen; and a pollen ejection device comprising a protruding member configured for puncturing the pollen pod to release a portion of the pollen.

15. The gardening appliance of claim 14, further comprising:

the pollen pod comprising a removable cover positioned over an opening of the pollen pod, wherein the pollen ejection device is configured for puncturing or removing the removable cover to release the pollen.

16. The gardening appliance of claim 14, further comprising the pollen pod, wherein the pollen pod is pressurized, and wherein the pollen ejection device is a puncturing device for breaking the pollen pod to release the pollen.

17. The gardening appliance of claim 14, further comprising the pollen pod, wherein the pollen pod comprises a permeable wall, and wherein the pollen ejection device comprises a source of compressed air to eject the pollen through the permeable wall.

18. The gardening appliance of claim 14, further comprising the pollen pod, wherein the pollen pod is positioned proximate a distal end of the grow module proximate the liner, and wherein the pollen ejection device is a protruding member extending from the liner for puncturing the pollen pod as it rotates past the protruding member.

19. The gardening appliance of claim 14, further comprising:

a motor mechanically coupled to the grow module for selectively rotating the grow module, wherein the motor selectively oscillates that grow module to discharge the pollen.

20. The gardening appliance of claim 14, further comprising:

the pollen pod; and an auxiliary air circulation device for circulating the pollen after the pollen is discharged from the pollen pod.

* * * * *